(12) United States Patent
Ackermann et al.

(10) Patent No.: US 7,999,130 B2
(45) Date of Patent: *Aug. 16, 2011

(54) METHODS FOR PRODUCING ALKYL(METH)ACRYLATES

(75) Inventors: Jochen Ackermann, Muehltal (DE);
Alexander May, Darmstadt (DE); Udo Gropp, Bad Endorf (DE); Hermann Siegert, Seeheim-Jugenheim (DE); Bernd Vogel, Wiesbaden (DE); Soenke Broecker, Ober-Ramstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 67 days.

This patent is subject to a terminal disclaimer.

(21) Appl. No.: 11/915,042

(22) PCT Filed: May 12, 2006

(86) PCT No.: PCT/EP2006/062281
§ 371 (c)(1),
(2), (4) Date: Nov. 20, 2007

(87) PCT Pub. No.: WO2006/122911
PCT Pub. Date: Nov. 23, 2006

(65) Prior Publication Data
US 2008/0194875 A1 Aug. 14, 2008

(30) Foreign Application Priority Data
May 20, 2005 (DE) .................. 10 2005 023 975

(51) Int. Cl.
*C07C 67/02* (2006.01)
(52) U.S. Cl. ........ 560/217; 560/129; 562/512; 562/598; 562/599
(58) Field of Classification Search ............ 562/512, 562/598, 599; 560/217, 129
See application file for complete search history.

(56) References Cited

U.S. PATENT DOCUMENTS

| 4,425,277 A * | 1/1984 | Kawamoto et al. ............ 554/153 |
|---|---|---|
| 4,458,088 A * | 7/1984 | Hardman et al. ............... 560/96 |
| 6,180,831 B1 | 1/2001 | Weber et al. |
| 6,596,251 B2 | 7/2003 | Schaefer et al. |
| 6,743,407 B2 | 6/2004 | Schaefer et al. |
| 6,977,310 B2 | 12/2005 | Ackermann et al. |
| 6,979,432 B2 | 12/2005 | Schaefer et al. |
| 7,288,402 B2 | 10/2007 | Osswald et al. |
| 7,429,370 B2 | 9/2008 | Von Hippel et al. |
| 7,491,521 B2 | 2/2009 | Osswald et al. |
| 2006/0211880 A1 | 9/2006 | Ackerman et al. |
| 2007/0149811 A1 | 6/2007 | Schleep et al. |
| 2007/0173664 A1 | 7/2007 | Krill et al. |
| 2008/0248538 A1 | 10/2008 | Osswald et al. |
| 2009/0118533 A1 | 5/2009 | Broell et al. |
| 2009/0149674 A1 | 6/2009 | Schleep et al. |

FOREIGN PATENT DOCUMENTS

| EP | 0 429 800 | 6/1991 |
|---|---|---|
| EP | 487853 A2 * | 6/1992 |
| GB | 341730 * | 1/1931 |

OTHER PUBLICATIONS

U.S. Appl. No. 11/914,493, filed Nov. 15, 2007, Ackermann, et al.
U.S. Appl. No. 11/995,206, filed Jan. 10, 2008, Sarcinelli, et al.
U.S. Appl. No. 60/893,788, filed Mar. 8, 2007, May, et al.
U.S. Appl. No. 12/298,034, filed Oct. 22, 2008, May, et al.
U.S. Appl. No. 12/300,189, filed Nov. 10, 2008, Broell, et al.
U.S. Appl. No. 12/299,217, filed Oct. 31, 2008, Broell, et al.
U.S. Appl. No. 12/307,773, filed Jan. 7, 2009, Ackermann, et al.
U.S. Appl. No. 12/441,145, filed Mar. 13, 2009, May, et al.
U.S. Appl. No. 12/515,036, filed May 15, 2009, May, et al.
U.S. Appl. No. 12/443,784, filed Mar. 31, 2009, Vogel, et al.
U.S. Appl. No. 12/442,215, filed Mar. 23, 2009, Vogel, et al.
U.S. Appl. No. 12/303,161, filed Dec. 2, 2008, Marx, et al.
U.S. Appl. No. 12/442,123, filed Mar. 20, 2009, Gropp, et al.
U.S. Appl. No. 12/516,629, filed May 28, 2009, Gropp, et al.
U.S. Appl. No. 12/517,366, filed Jun. 3, 2009, Gropp, et al.
U.S. Appl. No. 12/515,545, filed May 20, 2009, Gropp, et al.
U.S. Appl. No. 12/515,964, filed May 22, 2009, Gropp, et al.
U.S. Appl. No. 12/517,673, filed Jun. 4, 2009, Gropp, et al.
U.S. Appl. No. 12/517,199, filed Jun. 2, 2009, Gropp, et al.
U.S. Appl. No. 12/593,090, filed Sep. 25, 2009, Marx, et al.
U.S. Appl. No. 12/602,593, filed Dec. 1, 2009, Marx, et al.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The present invention relates to processes for preparing alkyl (meth)acrylates, comprising the steps of
transesterifying an alkyl α-hydroxycarboxylate with (meth)acrylic acid to obtain alkyl (meth)acrylates and α-hydroxycarboxylic acid, and dehydrating the α-hydroxycarboxylic acid to obtain (meth)acrylic acid.

22 Claims, 1 Drawing Sheet

METHODS FOR PRODUCING ALKYL(METH)ACRYLATES

CROSS-REFERENCE TO RELATED APPLICATIONS

The present application is a 35 U.S.C. §371 National Stage patent application of International patent application PCT/EP06/062281, filed on May 12, 2006, which claims priority to German patent application DE 102005023975.7, filed on May 20, 2005.

The present invention relates to processes for preparing alkyl (meth)acrylates.

Acrylic esters and methacrylic esters, referred to hereinafter as alkyl (meth)acrylates, find their main field of use in the preparation of polymers and copolymers with other polymerizable compounds.

Methacrylic ester, for example methyl methacrylate, is additionally an important monomer for various specialty esters based on methacrylic acid (MA), which are prepared by transesterification with the corresponding alcohol.

Methyl methacrylate (MMA) and methacrylic acid are today prepared predominantly starting from hydrocyanic acid and acetone via the acetone cyanohydrin (ACH) which is formed as a central intermediate.

Further processes which use a raw material basis other than ACH are described in the relevant patent literature and in the meantime have been realized on the production scale. In this connection, C-4 based raw materials such as isobutylene or tert-butanol are used today as reactants which are converted to the desired methacrylic acid derivatives via a plurality of process stages.

An additional subject of intensive investigation has been the use of propene as a base raw material, in which case methacrylic acid is obtained in moderate yields via the stages of hydrocarbonylation (to isobutyric acid) and dehydrogenating oxidation.

It is known that propanal or propionic acid which are obtainable in industrial processes starting from ethylene and C-1 units such as carbon monoxide can be used as the base raw material. In these processes, an aldolizing reaction with formaldehyde converts the β-hydroxycarbonyl compound formed in situ under dehydration to the corresponding α,β-unsaturated compound. An overview of the common processes for preparing methacrylic acid and esters thereof can be found in the literature such as Weissermel, Arpe "Industrielle organische Chemie" [Industrial organic chemistry], VCH, Weinheim 1994, 4th edition, p. 305 ff or Kirk Othmer "Encyclopedia of Chemical Technology", 3rd edition, Vol. 15, page 357.

It is commonly known that industrial processes based on ACH and using highly concentrated sulphuric acid (about 100% by weight $H_2SO_4$) in the first step of the reaction, known as the amidation, are carried out at temperatures between 80° C. and about 110° C.

A process representative of such a process is, for example, U.S. Pat. No. 4,529,816 in which the ACH amidation is carried out at temperatures of around 100° C. with a molar ratio of ACH:$H_2SO_4$ of from about 1:1.5 to 1:1.8. Relevant process steps for this process are: a) amidation; b) conversion; and c) esterification.

In the amidation, the main products obtained from the reaction are SIBAm=sulphoxy-alpha-hydroxyisobutyramide hydrogensulphate and MAA.$H_2SO_4$=methacrylamide hydrogensulphate as a solution in excess sulphuric acid. In addition, HIBAm.$H_2SO_4$=alpha-hydroxyisobutyramide hydrogensulphate is also obtained in a typical amidation solution with a yield based on ACH of <5%. At more or less complete ACH conversion, this amidation process which is quite selective per se proceeds with a yield (=sum of the intermediates described) of approx. 96-97%.

However, by-products formed in not inconsiderable amounts in this step are carbon monoxide, acetone, sulphonation products of acetone and cyclocondensation products of acetone with various intermediates.

The proportion of HIBAm as well as SIBAm in the amidation mixture is also established depending on the water content in the sulphuric acid used. When, for example, 97% by weight sulphuric acid (1.5 equivalents of $H_2SO_4$ based on ACH) is used, about 25% by weight of HIBAm forms and can no longer be selectively and fully reacted in the conversion to give MAA. The relatively high water content in the amidation at temperatures of 90° C.-110° C. thus results in a relatively high proportion of HIBAm which can be converted by conventional conversion only relatively unselectively to the target intermediate MAA.$H_2SO_4$.

The aim of the conversion is the substantially complete conversion of SIBAm and HIBAm to MAA which proceeds under β-elimination of sulphuric acid (in excess sulphuric acid as the solvent).

In the process step of conversion, the sulphuric acid (anhydrous) solution of HIBAm, SIBAm and MAA (each present as hydrogensulphates) is reacted at high temperatures between 140° C.-160° C. and short residence times of about 10 min or less.

The conversion mixture of this procedure is characterized by a high excess of sulphuric acid and the presence of the main product MAA.$H_2SO_4$ with a concentration in the solution of about 30-35% by weight (depending on the sulphuric acid excess used).

In the case of more or less complete SIBAm.$H_2SO_4$ reaction, the conversion step proceeds with an MAA.$H_2SO_4$ yield of approx. 94-95%. Adding the losses in the amidation as a result of the above-described side reactions, only between 90-92% MAA (based on ACH) is thus available for the subsequent esterification to the methyl methacrylate (MMA) desired as the product.

As a result of the severe reaction conditions, by-products which are formed in this process step are considerable amounts of condensation and addition products of the intermediates with one another.

The aim of the esterification is the substantially complete reaction of MAA.$H_2SO_4$ from the conversion to MMA. The esterification proceeds by addition of a mixture consisting of water and methanol to the MAA-sulphuric acid solution and proceeds at least partly via methacrylic acid (MA) as an intermediate. The reaction may be operated under pressure or at ambient pressure.

Typically, hydrolysis/esterification of the conversion solution at temperatures between 90° C.-140° C. at reaction times of one or more hours provide a sulphuric acid solution of MMA, MA and ammonium hydrogensulphate which has formed.

The reaction conditions in the presence of free sulphuric acid result in the methanol selectivity in this step being only about 90% or less, and dimethyl ether is formed as a by-product by condensation of methanol.

In the case of more or less complete MAA.$H_2SO_4$ reaction, the esterification proceeds with an MMA yield of approx. 98-99% based on MAA used (total selectivity of MA+MMA). Adding the losses in the amidation and the conversion as a result of the above-described side reactions, it is thus possible in the overall process over all stages to achieve maximum MMA yields of 90% based on ACH in an optimal reaction.

In addition to the poor overall yields of the above-described process which, especially on the production scale, are associated with the occurrence of considerable amounts of wastes and offgases, this process has the disadvantage that massively superstoichiometric amounts of sulphuric acid have to be used. From the ammonium hydrogensulphate- and sulphuric acid-containing process acid which is regenerated in a sulphuric acid contact plant, tarlike, solid condensation products additionally separate out and prevent trouble-free conveying of the process acid and have to be removed at considerable cost and inconvenience.

As a consequence of the drastic yield losses in the above-described process of U.S. Pat. No. 4,529,816, there are some proposals to amidate and hydrolyse ACH in the presence of water, in which case the hydroxyl function in the molecular unit is retained at least in the first steps of the reaction.

These proposals for an alternative amidation in the presence of water lead, depending on whether they are carried out in the presence of or without methanol, either to the formation of methyl 2-hydroxyisobutyrate (=MHIB) or to the formation of 2-hydroxyisobutyric acid (=HIBAc).

2-Hydroxyisobutyric acid is a central intermediate for the preparation of methacrylic acid and methacrylic esters derived therefrom, especially methyl methacrylate.

A further alternative for the preparation of esters of 2-hydroxyisobutyric acid, especially methyl 2-hydroxyisobutyrate, starting from ACH is described in JP Hei-4-193845. In JP Hei-4-193845, ACH is initially amidated below 60° C. with 0.8 to 1.25 equivalents of sulphuric acid in the presence of less than 0.8 equivalent of water and subsequently reacted at temperatures of greater than 55° C. with more than 1.2 equivalents of alcohol, especially methanol, to give MHIB or corresponding esters. No reference is made here to the presence of viscosity-lowering media which are stable toward the reaction matrix.

The disadvantages and problems of this process are the industrial implementation as a result of extreme viscosity formation at the end of the reaction.

Some approaches to the utilization and conversion of MHIB by dehydrating to give methyl methacrylate are described in the patent literature.

For example, in EP 0 429 800, MHIB or a mixture of MHIB and a corresponding alpha or beta-alkoxy ester is reacted in the gas phase, in the presence of methanol as a cofeed, over a heterogeneous catalyst consisting of a crystalline aluminosilicate and a mixed dopant composed of firstly an alkali metal element and secondly a noble metal. Even though conversion and selectivity of the catalyst are quite good at least at the start of the reaction, there is a quite drastic deactivation of the catalyst with increasing reaction time, which is associated with falling yields.

A similar approach is followed by EP 0 941 984, in which the gas phase dehydrogenation of MHIB is described as a substep of an MMA synthesis in the presence of a heterogeneous catalyst consisting of an alkali metal salt of phosphoric acid on $SiO_2$. However, this multistage process is complicated overall, entails elevated pressures and thus expensive equipment in substeps and only affords unsatisfactory yields.

In addition to the above-described studies on the dehydration of MHIB and related esters to the corresponding alpha-beta-unsaturated methacrylic acid compounds in the gas phase, there are also proposals to carry out the reaction in the liquid phase.

The preparation of MA starting from 2-hydroxyisobutyric acid is described, for example, in U.S. Pat. No. 3,487,101, where the preparation of various methacrylic acid derivatives, especially methacrylic acid and methacrylic esters, starting from 2-hydroxyisobutyric acid in the liquid phase, is characterized in that the reaction of HIBAc to give methacrylic acid is carried out in the presence of a dissolved basic catalyst at high temperatures between 180° C.-320° C. in the presence of high-boiling esters (e.g. dimethyl phthalate) and internal anhydrides (e.g. phthalic anhydride). According to the patent, MA selectivities of around 98% are achieved at HIBAc conversions of >90%. No information is given on the long-term stability of the liquid catalyst solution, especially the exhaustion of the anhydride used.

JP 184047/1985 also describes the dehydration of MHIB in the presence of highly concentrated sulphuric acid (90-100% by weight). Disadvantages in this case are the high input amounts of sulphuric acid and the inevitable occurrence of large amounts of aqueous sulphuric acid which are formed in the course of the reaction by the release of water from MHIB. Owing to the amounts of waste acid, this process is not gaining any economic importance.

DE-A 1 191367 relates to the preparation of methacrylic acid starting from 2-hydroxyisobutyric acid in the liquid phase, characterized in that the reaction of HIBAc to give methacrylic acid is carried out in the presence of polymerization inhibitors (for example copper powder) and in the presence of a catalyst mixture consisting of metal halides and alkali metal halides at high temperatures between 180-220° C. According to the patent, MA selectivities of >99% are achieved at HIBAc conversions of >90%. The best results are achieved with catalyst mixtures of zinc bromide and lithium bromide. It is commonly known that the use of halide-containing catalysts at high temperatures places drastic requirements on the materials to be used, and these problems relating to the halogenated entrained by-products in the distillate also occur in downstream parts of the plant.

EP 0 487 853 describes the preparation of methacrylic acid starting from acetone cyanohydrin, characterized in that, in the first step, ACH is reacted with water at moderate temperatures in the presence of a heterogeneous hydrolysis catalyst and, in the second step, 2-hydroxyisobutyramide is reacted with methyl formate or methanol/carbon monoxide to form formamide and methyl hydroxyisobutyrate, and, in the third step, MHIB is hydrolysed with water in the presence of a heterogeneous ion exchanger to give hydroxyisobutyric acid, and, in the fourth step, HIBAc is dehydrated by allowing it to react in the liquid phase at high temperatures in the presence of a soluble alkali metal salt. The methacrylic acid preparation from HIBAc is described at high conversions of around 99% with more or less quantitative selectivities. The multitude of reaction steps needed and the necessity of intermediately isolating individual intermediates, especially also the performance of individual process steps at elevated pressure, make the process complicated and thus ultimately uneconomic. In addition, formamide is necessarily used, and this compound in many cases has to be considered as an undesired by-product which has to be disposed of in an expensive manner.

DE-A 1 768 253 describes a process for preparing methacrylic acid by dehydrating alpha-hydroxyisobutyric acid, characterized in that HIBAc is reacted in the liquid phase at a temperature of at least 160° C. in the presence of a dehydration catalyst which consists of a metal salt of alpha-hydroxyisobutyric acid. Particularly suitable in this case are the alkali metal and alkaline earth metal salts of HIBAc which are prepared in an HIBAc melt by reacting suitable metal salts in situ. According to the patent, MA yields of up to 95% from HIBAc are described, the feed of the continuous procedure consisting of HIBAc and approx. 1.5% by weight of the alkali metal salt of HIBAc.

RU 89631 relates to a process for preparing methacrylic acid starting from 2-hydroxyisobutyric acid by elimination of water in the liquid phase, characterized in that the reaction is carried out in the absence of a catalyst with an aqueous solution of HIBAc (up to 62% by weight of HIBAc in water) under pressure at high temperatures of 200° C.-240° C. It is also known that 2-hydroxyisobutyric acid can be prepared starting from acetone cyanohydrin (ACH) by hydrolysing the nitrile function in the presence of mineral acids (see J. Brit. Chem. Soc. (1930); Chem. Ber. 72 (1939), 800).

A process representative of such a process is, for example, the Japanese patent publication Sho 63-61932, in which ACH is hydrolysed to 2-hydroxyisobutyric acid in a two-stage process. In this process, ACH is initially reacted in the presence of 0.2-1.0 mol of water and 0.5-2 equivalents of sulphuric acid to form the corresponding amide salts. Even in this step, the use of small concentrations of water and sulphuric acid which are needed to obtain good yields, short reaction times and small amounts of waste process acid, massive problems occur with the stirrability of the amidation mixture as a result of high viscosity of the reaction batches, especially towards the end of the reaction time.

When the molar amount of water is increased to ensure a low viscosity, the reaction slows drastically and side reactions occur, especially the fragmentation of ACH into the acetone and hydrocyanic acid reactants which react further under the reaction conditions to give subsequent products. According to the preliminary remarks of the Japanese patent publication SHO 63-61932, increasing the temperature does allow the viscosity of the reaction mixture to be controlled and the corresponding reaction batches to become stirrable as a result of the fall in viscosity, but here too the side reactions increase drastically even at moderate temperatures, which ultimately manifests itself in only moderate yields (see comparative examples).

When low temperatures of <50° C. which would ensure a selective reaction are employed, the increase towards the end of the reaction time in the concentration of the amide salts which are sparingly soluble under the reaction conditions results initially in the formation of a suspension which is difficult to stir and finally in the complete solidification of the reaction batch.

In the second step of the Japanese patent publication SHO 63-61932, water is added to the amidation solution and hydrolysis is effected at higher temperatures than the amidation temperature, in the course of which 2-hydroxyisobutyric acid is formed from the amide salts formed by the amidation to release ammonium hydrogensulphate.

Essential for the economic viability of an industrial process is not only the selective preparation of the HIBAc target product in the reaction, but also the isolation from the reaction matrix or the removal of HIBAc from the remaining process acid.

In JP Sho 57-131736, method for isolating alpha-oxyisobutyric acid (=HIBAc), this problem is treated by treating the reaction solution which is obtained after the reaction between acetone cyanohydrin, sulphuric acid and water by hydrolytic cleavage and comprises alpha-hydroxyisobutyric acid and acidic ammonium hydrogensulphate with an extractant, which transfers the 2-hydroxyisobutyric acid into the extractant and the acidic ammonium sulphate remains in the aqueous phase.

In this process, the free sulphuric acid remaining in the reaction medium is neutralized before the extraction by treating with an alkaline medium in order to increase the degree of extraction of HIBAc into the organic extraction phase. The necessary neutralization is associated with a considerable additional input of amine or mineral base and thus with considerable waste amounts of corresponding salts which cannot be disposed of in an ecologically and economically viable way.

The disadvantages of JP Sho 57-131736, process for preparing MMA via methacrylamide-hydrogensulphate (reaction sequence: amidation-conversion-hydrolytic esterification), can be summarized as follows:
   a.) Use of high molar sulphuric acid excesses based on ACH (in the industrial process, approx. 1.5-2 equivalents of sulphuric acid per equivalent of ACH)
   b.) High yield losses in the amidation step (approx. 3-4%) and in the conversion step (approx. 5-6%), which is ultimately manifested in a maximum methacrylamide sulphate yield of approx. 91%.
   c.) Large waste streams in the form of aqueous sulphuric acid in which ammonium hydrogensulphate and organic by-products are dissolved. Separation of undefined tar residues from this process waste acid which necessitate an aftertreatment or costly and inconvenient disposal.

The disadvantages of the JP Sho 57-131736 process for preparing MMA via hydroxyisobutyric acid as a central intermediate (reaction sequence: amidation-hydrolysis; HIBAc synthesis-MA synthesis-hydrolytic esterification) can be summarized as follows:
   a.) although low molar sulphuric acid excesses based on ACH (only approx. 1.0 equivalent of sulphuric acid per equivalent of ACH) are used, there are massive problems with viscosity and stirrability of the amidation medium up to complete solidification of the reaction batches; the proposed dilution of the amidation with alcohols (methanol) or various esters leads to incomplete ACH conversion under the reaction conditions, drastic increase in the side reactions or to chemical decomposition of the diluents;
   b.) high yield losses in the amidation step (approx. 5-6%) and complicated extraction with an organic solvent to form a water- and HIBAc-containing extractant phase which has to be worked up by distillation with high energy consumption to isolate HIBAc. About 2 kg of process acid waste are generated per kg of HIBAc and contain about 34% by weight of water as well as 66% by weight of ammonium hydrogensulphate (see Japanese publication SHO-57-131736, Example 4). The regeneration of a waste salt solution with high water contents in a sulphuric acid contact plant (=SC plant) is associated with considerable energy consumption which distinctly limits the capacity of such an SC plant.

It is common to all these processes that the isolation of HIBAc from the ammonium hydrogensulphate-containing aqueous reaction matrix is very costly and inconvenient. An excessively high water content in the HIBAc-containing extractant phase also causes entrainment of ammonium hydrogensulphate into the subsequent MA stage which can no longer be operated continuously on the industrial scale over an acceptable period. The high energy consumption in the regeneration of highly concentrated aqueous process acid and also extraction streams additionally make the proposed procedures uneconomic and they do not offer any real alternative to the established procedure which, although unselective, is appropriate to the purpose owing to the small number of simple process steps.

In view of the prior art, it was thus an object of the present invention to provide processes for preparing alkyl (meth) acrylates which can be carried out simply and inexpensively.

It is a further object of the present invention to provide a process in which the alkyl (meth)acrylates can be obtained very selectively.

Furthermore, it is therefore an object of the present invention to provide a process for preparing alkyl (meth)acrylates in which only a small amount of by-products is obtained. The product should be obtained in maximum yields and, viewed overall, with low energy consumption.

It is a further aim of the present invention to specify a process for preparing alkyl (meth)acrylates which can be realized particularly simply and inexpensively.

These and further objects which are not stated explicitly but which can be derived or discerned directly from the connections discussed by way of introduction herein are achieved by processes having all features of Patent Claim 1. Appropriate modifications of the processes according to the invention are protected in the subclaims dependent upon Claim 1.

The present invention accordingly provides processes for preparing alkyl (meth)acrylates, comprising the steps of transesterifying an alkyl α-hydroxycarboxylate with (meth) acrylic acid to obtain alkyl (meth)acrylates and α-hydroxycarboxylic acid, and dehydrating the α-hydroxycarboxylic acid to obtain (meth)acrylic acid.

The inventive measures may additionally achieve advantages including the following:

The process avoids the use of sulphuric acid in large amounts as a reactant. Accordingly, no large amounts of ammonium hydrogensulphate are obtained in the process according to the invention.

The process according to the invention affords the alkyl (meth)acrylates in high yields. This is true in particular in comparison with the processes described in EP-A-0941984, in which the alkyl α-hydroxycarboxylates are dehydrated directly to the alkyl (meth)acrylates. It was found that, surprisingly, the additional reaction step of transesterification of the alkyl α-hydroxycarboxylate with (meth)acrylic acid results in the achievement of higher selectivities overall.

In this reaction, the formation of by-products is unusually low. Moreover, especially taking into account the high selectivity, high conversions are achieved.

The process of the present invention has low formation of by-products.

The process according to the invention can be carried out inexpensively, especially with low energy demand. In this process, the catalysts used for dehydration and transesterification can be used over a long period without the selectivity or the activity decreasing.

The process of the present invention can be carried out on the industrial scale.

According to the invention, alkyl α-hydroxycarboxylates are reacted with (meth)acrylic acid. The (meth)acrylic acids useable for this purpose are known per se and can be obtained commercially. In addition to acrylic acid (propenoic acid) and methacrylic acid (2-methylpropenoic acid), these include in particular derivatives which comprise substituents. The suitable substituents include in particular halogens such as chlorine, fluorine and bromine, and also alkyl groups which may preferably comprise from 1 to 10, more preferably from 1 to 4 carbon atoms. These include β-methylacrylic acid (butenoic acid), α,β-dimethylacrylic acid, β-ethylacrylic acid, and β,β-dimethylacrylic acid. Preference is given to acrylic acid (propenoic acid) and methacrylic acid (2-methylpropenoic acid), particular preference being given to methacrylic acid.

The alkyl α-hydroxycarboxylates used for this purpose are known per se, the alcohol radical of the ester comprising preferably from 1 to 20 carbon atoms, in particular from 1 to 10 carbon atoms and more preferably from 1 to 5 carbon atoms. Preferred alcohol radicals derive in particular from methanol, ethanol, propanol, butanol, in particular n-butanol and 2-methyl-1-propanol, pentanol, hexanol and 2-ethylhexanol, particular preference being given to methanol and ethanol.

The acid radical of the alkyl α-hydroxycarboxylates used for the transesterification derives preferably from the (meth) acrylic acid which can be obtained by dehydrating the α-hydroxycarboxylic acid. When, for example, methacrylic acid is used, α-hydroxyisobutyric ester is used. When, for example, acrylic acid is used, preference is given to using α-hydroxyisopropionic acid.

Alkyl α-hydroxycarboxylates used with preference are methyl α-hydroxypropionate, ethyl α-hydroxypropionate, methyl α-hydroxyisobutyrate and ethyl α-hydroxyisobutyrate.

Such alkyl α-hydroxycarboxylates are in many cases obtained inexpensively from the corresponding cyanohydrins. In this context, the purity of the cyanohydrin is uncritical. Accordingly, purified or unpurified cyanohydrin can be used for the hydrolysis reaction. Accordingly, the alkyl α-hydroxycarboxylates to be used in accordance with the invention may be obtained from ketones and aldehydes, and also hydrocyanic acid and a corresponding alcohol.

In a first step, the carbonyl compound, for example a ketone, in particular acetone, or an aldehyde, for example acetaldehyde, propanal, butanal, is reacted with hydrocyanic acid to give the corresponding cyanohydrin. Particular preference is given here to reacting acetone and/or acetaldehyde in a typical manner using a small amount of alkali or of an amine as a catalyst.

In a further step, the cyanohydrin thus obtained is reacted with water to give the hydroxycarboxamide.

Typically, this reaction is carried out in the presence of a catalyst. Suitable catalysts for this purpose are in particular manganese oxide catalysts, as described, for example, in EP-A-0945429, EP-A-0561614 and EP-A-0545697. In this case, the manganese oxide may be used in the form of manganese dioxide which is obtained by treating manganese sulphate with potassium permanganate under acidic conditions (cf. Biochem. J., 50 p. 43 (1951) and J. Chem. Soc., 1953, p. 2189, 1953) or by electrolytic oxidation of manganese sulphate in aqueous solution. In general, the catalyst is in many cases used in the form of powder or granules with a suitable particle size. In addition, the catalyst may be applied to a support. In this case, it is in particular also possible to use slurry reactors or fixed bed reactors, which are described, inter alia, in EP-A-956 898.

In addition, the hydrolysis reaction may be catalysed by enzymes. The suitable enzymes include nitrile hydratases. This reaction is described by way of example in "Screening, Characterization and Application of Cyanide-resistant Nitrile Hydratases" Eng. Life. Sci. 2004, 4, No. 6.

In addition, the hydrolysis reaction may be catalysed by acids, in particular sulphuric acid. This is stated, inter alia, in JP Hei 4-193845.

The water which is needed for the hydrolysis of the cyanohydrin can in many cases be used as a solvent. The molar ratio of water to cyanohydrin is preferably at least 1; the molar ratio of water to cyanohydrin is more preferably in the range of 0.5:1-25:1 and most preferably in the range of 1:1-10:1.

The water used for the hydrolysis may have a high purity. However, this property is not obligatory. Thus, as well as fresh water, it is also possible to use service water or process water which comprises greater or lesser amounts of impurities. Accordingly, it is also possible to use recycled water for the hydrolysis.

In addition, further constituents may be present in the reaction mixture for the hydrolysis of the cyanohydrin. These include aldehydes and ketones, especially those which have been used to prepare the cyanohydrin. For example, acetone and/or acetaldehyde may be present in the reaction mixture. This is stated, for example, in U.S. Pat. No. 4,018,829-A. The purity of the aldehydes and/or ketones added is generally not particularly critical. Accordingly, these substances may comprise impurities, in particular alcohols, for example methanol, water and/or methyl α-hydroxyisobutyrate (MHIB). The amount of carbonyl compounds, especially acetone and/or acetaldehyde, may be used within wide ranges in the reaction mixture. The carbonyl compound is preferably used in an amount of 0.1-6 mol, preferably 0.1-2 mol per mole of cyanohydrin.

The temperature at which the hydrolysis reaction is effected may generally be in the range of 10-150° C., preferably in the range of 20-100° C. and more preferably in the range of 30-80° C.

The reaction can, for example, be carried out in a fixed bed reactor or in a suspension reactor.

The reaction mixture thus obtained comprises generally, in addition to the desired hydroxy amide, further constituents, in particular unconverted cyanohydrin and possibly acetone and/or acetaldehyde used. Accordingly, the reaction mixture can be purified, which cleaves unconverted cyanohydrin into acetone and hydrocyanic acid in order to reuse them for the preparation of cyanohydrin. The same applies to the acetone and/or acetaldehyde removed.

In addition, the purified reaction mixture comprising hydroxy amide can be purified to free it of further constituents by ion exchange columns.

For this purpose, especially cation exchangers and anion exchangers may be used. Ion exchangers suitable for this purpose are known per se. For example, suitable cation exchangers can be obtained by sulphonation of styrene-divinylbenzene copolymers. Basic anion exchangers comprise quaternary ammonium groups which are bonded covalently to styrene-divinylbenzene copolymers.

The steps for the preparation of α-hydroxycarboxamides are described in detail, inter alia, in EP-A-0686623.

In the next step, the α-hydroxycarboxamide thus obtained can be converted to the alkyl α-hydroxycarboxylate. This can be done, for example, by the use of alkyl formates. Methyl formate or a mixture of methanol and carbon monoxide are especially suitable, and this reaction is described by way of example in EP-A-0407811.

The α-hydroxycarboxamide is preferably converted by alcoholysis with an alcohol which comprises preferably 1-10 carbon atoms, more preferably 1 to 5 carbon atoms. Preferred alcohols include methanol, ethanol, propanol, butanol, in particular n-butanol and 2-methyl-1-propanol, pentanol, hexanol, heptanol, 2-ethylhexanol, octanol, nonanol and decanol. The alcohol used is more preferably methanol and/or ethanol, very particular preference being given to methanol.

The reaction of carboxamides with alcohols to obtain carboxylic esters is common knowledge.

This reaction can be accelerated, for example, by basic catalysts. These include homogeneous catalysts and heterogeneous catalysts.

The homogeneous catalysts include alkali metal alkoxides and organometallic compounds of titanium, tin and aluminium. Preference is given to using a titanium alkoxide or tin alkoxide, for example titanium tetraisopropoxide or tin tetrabutoxide. The heterogeneous catalysts include magnesium oxide, calcium oxide and basic ion exchangers as have been described above.

The molar ratio of α-hydroxycarboxamide to alcohol, for example α-hydroxyisobutyramide to methanol, is not critical per se, but is preferably in the range of 2:1-1:20.

The reaction temperature may likewise be within wide ranges, the reaction rate generally increasing with increasing temperature. The upper temperature limit generally arises from the boiling point of the alcohol used. The reaction temperature is preferably in the range of 40-300° C., more preferably 160-240° C. Depending on the reaction temperature, the reaction may be carried out at reduced or elevated pressure. This reaction is preferably carried out in a pressure range of 0.5-35 bar, more preferably 5 to 30 bar.

Typically, the ammonia formed is passed out of the reaction system, the reaction in many cases being carried out at the boiling point.

The ammonia released in the alcoholysis can be returned to the overall process in a simple manner. For example, ammonia can be reacted with methanol to give hydrocyanic acid. This is stated, for example, in EP-A-0941984. In addition, the hydrocyanic acid can be obtained from ammonia and methane according to the BMA or Andrussow process, these processes being described in Ullmann's Encyclopedia of Industrial Chemistry $5^{th}$ edition on CD-ROM, under "Inorganic Cyano Compounds".

In a next step, the alkyl α-hydroxycarboxylate is reacted with (meth)acrylic acid to obtain alkyl (meth)acrylate and α-hydroxycarboxylic acid.

In addition to the reactants, the reaction mixture may comprise further constituents, for example solvents, catalysts, polymerization inhibitors and water.

The reaction of the alkyl hydroxycarboxylate with (meth) acrylic acid can be catalysed by at least one acid or at least one base. It is possible here to use either homogeneous or heterogeneous catalysts. Particularly suitable catalysts are in particular inorganic acids, for example sulphuric acid or hydrochloric acid, and organic acids, for example sulphonic acids, in particular p-toluenesulphonic acid, and acidic cation exchangers.

The particularly suitable cation exchange resins include in particular sulphonic acid-containing styrene-divinylbenzene polymers. Particularly suitable cation exchange resins can be obtained commercially from Rohm & Haas under the trade name Amberlyst® and from Bayer under the trade name Lewatit®.

The concentration of catalyst is preferably in the range from 1 to 30% by weight, more preferably 5 to 15% by weight, based on the total of the alkyl α-hydroxycarboxylate used and of the (meth)acrylic acid used.

The polymerization inhibitors useable with preference include phenothiazine, tert-butylcatechol, hydroquinone monomethyl ether, hydroquinone, 4-hydroxy-2,2,6,6-tetramethylpiperidinooxyl (TEMPOL) or mixtures thereof; the effectiveness of some of these inhibitors being improvable by the use of oxygen. The polymerization inhibitors may be used in a concentration in the range from 0.001 to 2.0% by weight, more preferably in the range from 0.01 to 0.2% by weight, based on the total of the alkyl α-hydroxycarboxylate used and of the (meth)acrylic acid used.

The reaction is carried out preferably at temperatures in the range from 50° C. to 200° C., more preferably 70° C. to 130° C., in particular 80° C. to 120° C. and most preferably 90° C. to 110° C.

The reaction can be carried out at reduced or elevated pressure depending on the reaction temperature. This reaction is preferably carried out in the pressure range of 0.02-5 bar, in particular 0.2 to 3 bar and more preferably 0.3 to 0.5 bar.

The molar ratio of (meth)acrylic acid to the alkyl α-hydroxycarboxylate is preferably in the range from 4:1-1:4, in particular 3:1 to 1:3 and more preferably in the range from 2:1-1:2.

The selectivity is preferably at least 90%, more preferably 98%. The selectivity is defined as the ratio of the sum of amounts of alkyl (meth)acrylates and α-hydroxycarboxylic acids formed, based on the sum of the amounts of alkyl α-hydroxycarboxylate and (meth)acrylic acid converted.

In a particular aspect of the present invention, the transesterification can be effected in the presence of water. The water content is preferably in the range of 0.1-50% by weight, more preferably 0.5-20% by weight and most preferably 1-10% by weight, based on the weight of the alkyl α-hydroxycarboxylate used.

The addition of small amounts of water surprisingly allows the selectivity of the reaction to be increased. In spite of addition of water, the formation of methanol can be kept surprisingly low. At a water concentration of 10 to 15% by weight, based on the weight of the alkyl α-hydroxycarboxylate used, preferably less than 5% by weight of methanol are formed at a reaction temperature of 120° C. and a reaction time or residence time of 5 to 180 min.

The transesterification can be carried out batchwise or continuously, preference being given to continuous processes.

The reaction time of the transesterification depends upon the molar masses used and the reaction temperature, these parameters lying within wide ranges. The reaction time of the transesterification of the alkyl α-hydroxycarboxylate with (meth)acrylic acid is preferably in the range from 30 seconds to 15 hours, more preferably 5 minutes to 5 hours and most preferably 15 minutes to 3 hours.

In continuous processes, the residence time is preferably 30 seconds to 15 hours, more preferably 5 minutes to 5 hours and most preferably 15 minutes to 3 hours.

When methyl methacrylate is prepared from methyl α-hydroxyisobutyrate, the temperature is preferably 60 to 130° C., more preferably 80 to 120° C. and most preferably 90 to 110° C. The pressure is preferably in the range from 50 to 1000 mbar, more preferably 300 to 800 mbar. The molar ratio of methacrylic acid to methyl α-hydroxyisobutyrate is preferably in the range of 2:1-1:2, in particular 1.5:1-1:1.5.

Figure 1:
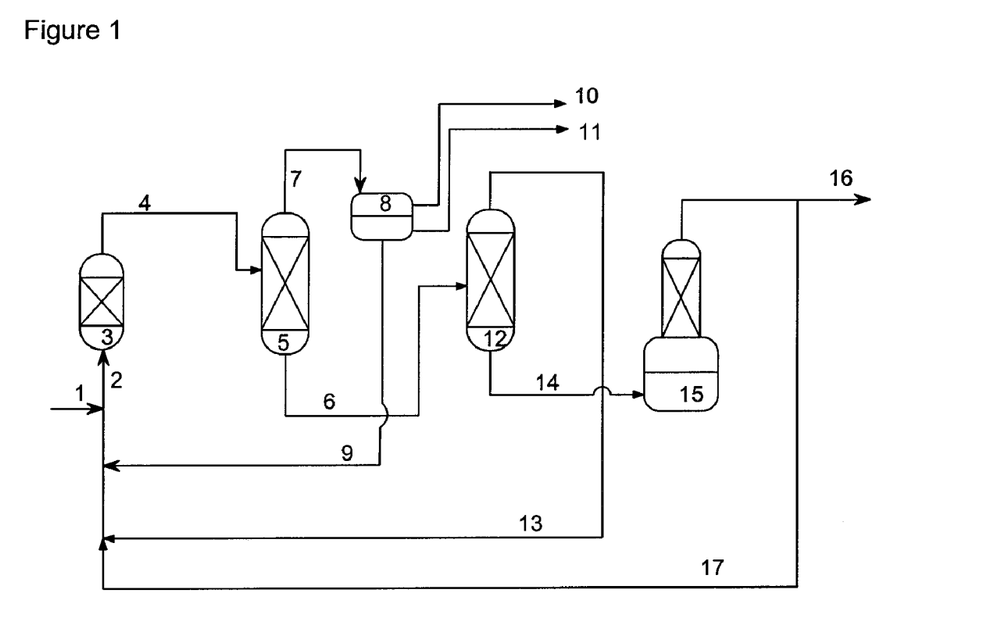
FIG. 1 shows a scheme of a plant in which the process of the present invention can be performed.

For example, the transesterification can be effected in the plant shown in FIG. 1. The hydroxycarboxylic ester, for example methyl hydroxyisobutyrate, is fed via line (1) to a fixed bed reactor (3) which comprises a cation exchange resin. (Meth)acrylic acid, for example 2-methylpropenoic acid, is added via line (2) or line (17) into the fixed bed reactor (3). Line (2) may be connected to further lines, for example line (9) and line (13), in order thus to reduce the number of feed lines into the reactor. Lines (9), (13) and/or (17) may, however, also lead directly into the fixed bed reactor. Under the aforementioned reaction conditions, a reaction mixture is formed which comprises, in addition to methanol and unconverted methyl hydroxyisobutyrate and methacrylic acid, the reaction products hydroxyisobutyric acid and methyl methacrylate. This reaction mixture is passed via line (4) into a still (5). In the still (5), water, methyl methacrylate and methanol are obtained as a distillate which is fed via line (7) as the top product to a phase separator (8). In the upper phase, methyl methacrylate and methanol collect and are withdrawn from the system via line (10). In the lower phase of the phase separator (8), water in particular collects and is removed from the system via line (11) or can be fed to the fixed bed reactor (3) via line (9).

From the bottom, methyl hydroxyisobutyrate, hydroxyisobutyric acid and methacrylic acid can be obtained and can be passed via line (6) into a second still (12). Here, methyl hydroxyisobutyrate and methacrylic acid are distilled off and recycled via line (13) to the transesterification. The hydroxyisobutyric acid present in the distillation bottoms are passed via line (14) into a reactor for dehydration (15). The methacrylic acid obtained in this way can be fed via line (17) to the transesterification explained above or withdrawn from the system via line (16).

In a particularly preferred embodiment, the transesterification can be effected in a still. In this case, the catalyst can be added in any region of the still. For example, the catalyst may be provided in the region of the bottom or in the region of the column. However, the reactants should be brought into contact with the catalyst. Moreover, catalyst can be provided in a separate region of the still, this region being connected to the further regions of the still, for example of the bottom and/or of the column. This separate arrangement of the catalyst region is preferred.

As a result of this preferred embodiment, it is surprisingly possible to increase the selectivity of the reaction. In this context, it should be emphasized that the pressure of the reaction can be adjusted independently of the pressure within the distillation columns. As a result, the boiling temperature can be kept low without the reaction time or the residence time rising correspondingly. In addition, the temperature of the reaction can be varied over a wide range. This allows the reaction time to be shortened. In addition, the volume of catalyst can be selected as desired without having to take account of the geometry of the column. Moreover, it is possible, for example, to add a further reactant. All of these measures can contribute to an increase in the selectivity and the productivity, and surprising synergistic effects are achieved.

The alkyl α-hydroxycarboxylate, for example methyl α-hydroxyisobutyrate, is fed to the still. Additionally introduced into the still is (meth)acrylic acid, for example methacrylic acid. The distillation conditions are preferably such that exactly one product is passed out of the still by distillation, the second product remaining in the bottom and being removed continuously therefrom. When alcohols with a small number of carbon atoms are used, in particular ethanol or methanol, the alkyl (meth)acrylate is preferably withdrawn from the reaction mixture by distillation. The reactants are passed cyclically through the catalyst region. This continuously forms alkyl (meth)acrylate and α-hydroxycarboxylic acid.

Figure 2:
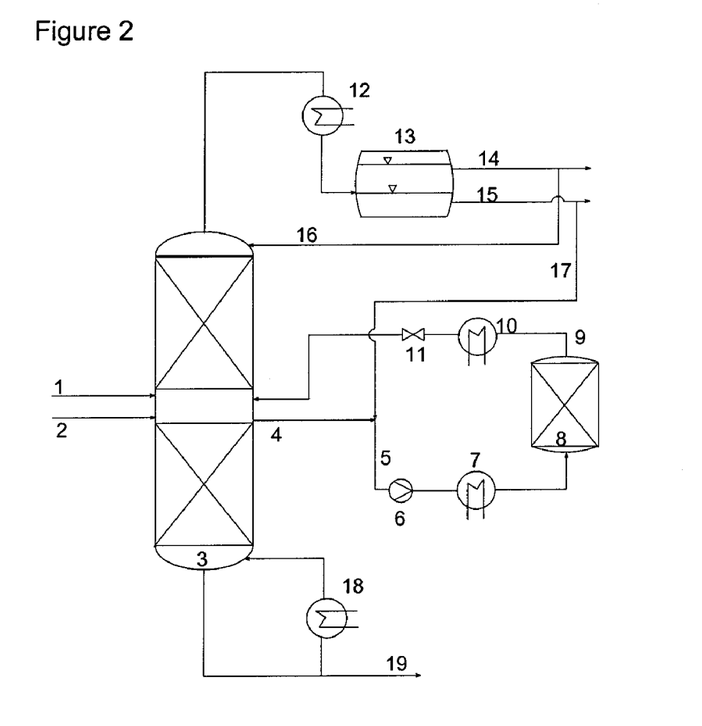
FIG. 2 shows a scheme of the reactive distillation.

A preferred embodiment of the reactive distillation is shown schematically in FIG. 2. The reactants may be introduced into the distillation column (3) via one common line (1) or separately via two lines (1) and (2). The reactants are preferably added via separate lines. The reactants can be fed at the same stage or in any position in the column.

The temperature of the reactants can be adjusted by means of a heat exchanger in the feed, the units needed for this purpose not being shown in FIG. 1. In a preferred variant, the reactants are metered separately into the column, the lower-boiling components being metered in below the position for the feeding of the higher-boiling compound. In this case, the lower-boiling component is preferably added in vaporous form.

For the present invention, any multistage distillation column (3) may be used which has two or more separating stages. The number of separating stages used in the present invention is the number of trays in a tray column or the number of theoretical plates in the case of a column with structured packing or a column with random packings.

Examples of a multistage distillation column with trays include those having bubble-cap trays, sieve trays, tunnel-cap trays, valve trays, slot trays, slotted sieve trays, bubble-cap sieve trays, jet trays, centrifugal trays; for a multistage distillation column with random packings, those such as Raschig rings, Lessing rings, Pall rings, Berl saddles, Intalox saddles; and, for a multistage distillation column with structured packings, those such as Mellapak (Sulzer), Rombopak (Kühni), Montz-Pak (Montz) and structured packings with catalyst pockets, for example Kata-Pak.

A distillation column with combinations of regions of trays, of regions of random packings or of regions of structured packings may likewise be used.

The column (3) may be equipped with internals. The column preferably has a condenser (12) for condensing the vapour and a bottom evaporator (18).

The distillation apparatus preferably has at least one region, known hereinafter as reactor, in which at least one catalyst is provided. This reactor may be within the distillation column. However, this reactor is preferably arranged outside the column (3) in a separate region, one of these preferred embodiments being explained in detail in FIG. 2.

In order to carry out the transesterification reaction in a separate reactor (8), it is possible within the column to collect a portion of the liquid phase flowing downwards by means of a collector and to pass it out of the column as a substream (4). The position of the collector is determined by the concentration profile in the column of the individual components. The concentration profile can be regulated by means of the temperature and/or the reflux. The collector is preferably positioned such that the stream conducted out of the column contains both reactants, more preferably the reactants in sufficiently high concentration and most preferably in a molar acid:ester ratio=1.5:1 to 1:1.5. In addition, a plurality of collectors may be provided at various points in the distillation column, in which case the amount of reactants withdrawn can be used to adjust the molar ratios.

It is additionally possible for a further reactant, for example water, to be metered into the stream conducted out of the column, in order to adjust the acid/ester product ratio in the cross-transesterification reaction or to increase the selectivity. The water can be fed from outside via a line (not shown in FIG. 1) or from a phase separator (13). The pressure of the stream (5) enriched with water can then be increased by a means for pressure increase (6), for example a pump.

An increase in the pressure can reduce or prevent formation of steam in the reactor, for example a fixed bed reactor. This allows uniform flowthrough of the reactor and wetting of the catalyst particles. The stream can be conducted through a heat exchanger (7) and the reaction temperature adjusted. The stream can be heated or cooled as required. It is additionally possible to adjust the ester to acid product ratio via the reaction temperature.

The transesterification reaction takes place over the catalyst in the fixed bed reactor (8). The flow through the reactor may be downwards or upwards. The reactor output stream (9) comprising the products and the unconverted reactants to a certain degree, the content of the components in the reactor waste stream depending upon the residence time, the catalyst mass, the reaction temperature and the reactant ratio and the amount of water added, is first passed through a heat exchanger (10) and adjusted to a temperature which is advantageous for the introduction into the distillation column. Preference is given to setting the temperature which corresponds to the temperature in the distillation column at the point of introduction of the stream.

The position where the stream leaving the reactor is returned into the column may lie above or below the position for the withdrawal of the reactor feed, but will preferably be above it. Before the recycling into the column, the stream may be decompressed through a valve (11), which preferably establishes the same pressure level as in the column. In this context, the distillation column preferably has a lower pressure. This configuration offers the advantage that the boiling points of the components to be separated are lower, as a result of which the distillation can be carried out at a lower temperature level, as a result of which it saves energy and is more thermally gentle.

In the distillation column (3), the product mixture is then separated. The low boiler, preferably the ester formed in the transesterification, is removed via the top. The distillation column is preferably operated such that the water added upstream of the fixed bed reactor is likewise removed as the top product. The vaporous stream drawn off at the top is condensed in a condenser (12) and then separated in a decanter (13) into the aqueous phase and product ester-containing phase. The aqueous phase can be discharged to the workup via a line (15) or returned fully or partly back into the reaction as a stream via line (17). The stream of the ester-containing phase can be conducted via line (14) partly as reflux (16) to the column or discharged partly from the still. The high boiler, preferably the acid formed in the cross-transesterification, is discharged from the column (19) as a bottom stream.

As a result of this preferred embodiment, it is surprisingly possible to increase the selectivity of the reaction. In this connection, it should be emphasized that the pressure of the reaction can be adjusted independently of the pressure within the distillation columns. As a result of this, the boiling temperature can be kept low without the reaction time or the residence time rising correspondingly. In addition, the temperature of the reaction can be varied over a wide range. As a result of this, the reaction time can be shortened. In addition, the volume of catalyst can be selected as desired without having to take account of the geometry of the column. Moreover, for example, a further reactant can be added.

The α-hydroxycarboxylic acid obtained from the reaction, for example hydroxyisobutyric acid, can be dehydrated in a known manner. In general, the α-hydroxycarboxylic acid, for example the α-hydroxyisobutyric acid, is heated in the presence of at least one metal salt, for example of alkali metal and/or alkaline earth metal salts, to temperatures in the range of 160-300° C., more preferably in the range of 200 to 240° C., to generally obtain the (meth)acrylic acid and water. The suitable metal salts include sodium hydroxide, potassium hydroxide, calcium hydroxide, barium hydroxide, magnesium hydroxide, sodium sulphite, sodium carbonate, potassium carbonate, strontium carbonate, magnesium carbonate, sodium bicarbonate, sodium acetate, potassium acetate and sodium dihydrogenphosphate.

The dehydration of the α-hydroxycarboxylic acid can be carried out preferably at a pressure in the range from 0.05 bar to 2.5 bar, more preferably in the range from 0.1 bar to 1 bar.

In a particular aspect of the present invention, the pressure in the dehydration is approximately equal to the pressure in the above-described transesterification of the alkyl α-hydroxycarboxylate with the (meth)acrylic acid, without any intention that this should impose a restriction. The difference of the pressure in the transesterification and the dehydration is preferably less than 0.1 bar, more preferably less than 0.05 bar. In a particular embodiment of the present invention, the (meth)acrylic acid obtained in gaseous form can be passed to the transesterification without condensation and reevaporation.

The dehydration of α-hydroxycarboxylic acids is described, for example, in DE-A-176 82 53.

The (meth)acrylic acid thus obtained can be used in turn to prepare alkyl (meth)acrylates. In addition, (meth)acrylic acid is a commercial product. Surprisingly, it is accordingly possible for the plant for preparing alkyl (meth)acrylates likewise to serve for the preparation of (meth)acrylic acid, in which case the product ratio of alkyl (meth)acrylates to (meth) acrylic acid can be regulated easily by the concentration of water in the transesterification of the alkyl α-hydroxycarboxylate and/or by the reaction temperature.

Overall, it is thus possible to obtain alkyl (meth)acrylates from carbonyl compounds, hydrocyanic acid and alcohols in a simple and inexpensive manner by processes which comprise the following steps:

A) formation of at least one cyanohydrin by reacting at least one carbonyl compound with hydrocyanic acid;

B) hydrolysis of the cyanohydrin or of the cyanohydrins to form at least one α-hydroxycarboxamide;

C) alcoholysis of the α-hydroxycarboxamide or of the α-hydroxycarboxamides to obtain at least one alkyl α-hydroxycarboxylate;

D) transesterification of the alkyl α-hydroxycarboxylate or of the alkyl α-hydroxycarboxylates with (meth)acrylic acid to form at least one alkyl (meth)acrylate and at least one α-hydroxycarboxylic acid;

E) dehydration of the α-hydroxycarboxylic acid or of the α-hydroxycarboxylic acids to form (meth)acrylic acid.

The present invention will be illustrated in detail hereinafter with reference to examples and to a comparative example.

EXAMPLE 1

In a reactive still shown in FIG. 2, 4619 g of methyl α-hydroxyisobutyrate (MHIB) and 3516 g of methacrylic acid (MA) were fed in over a period of 48 hours. The reaction was carried out at a temperature of 120° C. and a pressure of 250 mbar. α-Hydroxyisobutyric acid formed was removed from the bottom. Methyl methacrylate (MMA) was distilled off. The reaction was carried out in the presence of 16% by weight of water based on the weight of methyl α-hydroxyisobutyrate. The reaction was carried out using an acidic catalyst (cation exchanger; Lewatit® K2431 from Bayer).

The selectivity, defined as the ratio of amounts of methyl methacrylate (MMA) and α-hydroxyisobutyric acid (HIBAc) formed to amounts of MHIB and MA converted, was 99%.

The α-hydroxyisobutyric acid obtained from the process was dehydrated according to DE-A 17 68 253.

Overall, a selectivity of 98.5% is calculated, which is defined as the ratio of amount of MMA formed to amount of MHIB formed.

COMPARATIVE EXAMPLE 1

Methyl methacrylate was prepared by dehydrating methyl α-hydroxyisobutyrate. This reaction was carried out according to EP-A-0941984. A mixture of 20 g of sodium dihydrogenphosphate and 80 g of water was added to 60 g of silica gel. The water was removed from the mixture under a reduced pressure. The residue was dried at 150° C. overnight to obtain a catalyst. 10 g of the catalyst obtained were introduced into a quartz tube which was equipped with an evaporator. The quartz tube was heated with an oven, the temperature of the catalyst layer being about 400° C. A mixture of methanol and methyl α-hydroxyisobutyrate (2:1) was evaporated continuously at a rate of 10 g per hour and passed through the catalyst layer. The selectivity, defined as the ratio of amount of MMA formed to the amount of MHIB converted, of the reaction was 88%.

EXAMPLES 2 to 18

Example 1 was essentially repeated, except that no water was added to the reaction mixture. The reaction was effected under the conditions specified in Table 1, especially with regard to temperature, residence time and molar ratio of the reactants. The selectivity, defined as the ratio of amounts of MMA and HIBAc formed to amounts of MHIB and MA converted, of the reactions is likewise shown in Table 1.

TABLE 1

| Example | Reaction temperature [° C.] | Molar MHIB/MA ratio | Residence time [min] | Selectivity [%] |
|---|---|---|---|---|
| 2 | 120 | 1.00 | 28.33 | 93.21 |
| 3 | 90 | 1.00 | 42.50 | 95.06 |
| 4 | 100 | 1.00 | 42.50 | 94.81 |
| 5 | 110 | 1.00 | 42.50 | 94.64 |
| 6 | 120 | 1.00 | 42.50 | 90.67 |
| 7 | 90 | 1.00 | 85.00 | 95.53 |
| 8 | 100 | 1.00 | 85.00 | 94.95 |
| 9 | 110 | 1.00 | 85.00 | 93.55 |
| 10 | 120 | 1.00 | 85.00 | 91.78 |
| 11 | 90 | 1.00 | 170.00 | 94.83 |
| 12 | 100 | 1.00 | 170.00 | 94.06 |
| 13 | 90 | 2.0 | 42.50 | 91.61 |
| 14 | 100 | 2.0 | 42.50 | 91.73 |
| 15 | 90 | 2.0 | 85.00 | 90.63 |
| 16 | 100 | 2.0 | 85.00 | 90.30 |
| 17 | 120 | 0.50 | 28.33 | 92.05 |
| 18 | 120 | 0.50 | 42.50 | 92.62 |

EXAMPLES 19 to 38

Example 1 was essentially repeated, except that the reaction was carried out under the conditions specified in Table 2, especially with regard to the temperature and residence time. The molar ratio of MHIB/MA was 1:1. In addition, different proportions of water were added, which are likewise listed in Table 2. The selectivity, defined as the ratio of amounts of MMA and HIBAc formed to amounts of MHIB and MA converted, of the reactions and the molar ratio of HIBAc to MMA are likewise listed in Table 2.

TABLE 2

| Ex. | Reaction temperature [° C.] | Molar $H_2O$ to MHIB ratio | Residence time [min] | Selectivity [%] | Molar HIBAc to MMA ratio |
|---|---|---|---|---|---|
| 19 | 90 | 0.20 | 42.5 | 98.61 | 1.33 |
| 20 | 100 | 0.20 | 42.5 | 98.18 | 1.21 |
| 21 | 110 | 0.20 | 42.5 | 97.44 | 1.11 |
| 22 | 120 | 0.20 | 42.5 | 96.27 | 0.99 |

TABLE 2-continued

| Ex. | Reaction temperature [° C.] | Molar H₂O to MHIB ratio | Residence time [min] | Selectivity [%] | Molar HIBAc to MMA ratio |
|---|---|---|---|---|---|
| 23 | 90 | 0.20 | 85 | 98.34 | 1.18 |
| 24 | 100 | 0.20 | 85 | 97.66 | 1.09 |
| 25 | 110 | 0.20 | 85 | 96.56 | 1.02 |
| 26 | 100 | 0.20 | 170 | 96.95 | 1.00 |
| 27 | 90 | 0.50 | 42.5 | 98.80 | 1.61 |
| 28 | 100 | 0.50 | 42.5 | 98.64 | 1.36 |
| 29 | 110 | 0.50 | 42.5 | 98.21 | 1.22 |
| 30 | 120 | 0.50 | 42.5 | 97.58 | 1.08 |
| 31 | 90 | 0.50 | 85 | 98.76 | 1.39 |
| 32 | 100 | 0.50 | 85 | 98.35 | 1.20 |
| 33 | 110 | 0.50 | 85 | 97.78 | 1.10 |
| 34 | 100 | 0.50 | 170 | 98.08 | 1.10 |
| 35 | 90 | 1.00 | 50.0 | 99.41 | 2.090 |
| 36 | 100 | 1.00 | 50.0 | 99.65 | 1.618 |
| 37 | 110 | 1.00 | 50.0 | 99.82 | 1.360 |
| 38 | 120 | 1.00 | 50.0 | 99.54 | 1.319 |

The above examples show that, by virtue of the present invention, it is possible to form alkyl (meth)acrylates with very high selectivity, the ratio of alkyl (meth)acrylates to α-hydroxycarboxylic acid, even at relatively high water concentrations, being close to 1. Accordingly, relatively little methanol is formed. The molar ratio of alkyl (meth)acrylates to α-hydroxycarboxylic acid can also be controlled via the temperature.

The invention claimed is:

1. A process for preparing an alkyl (meth)acrylate, comprising:
    transesterifying an alkyl α-hydroxycarboxylate with a (meth)acrylic acid to obtain the alkyl (meth)acrylate and an α-hydroxycarboxylic acid, and
    dehydrating the α-hydroxycarboxylic acid to obtain a (meth)acrylic acid,
    wherein the transesterification comprises from 0.1 to 50% water by weight relative to the alkyl α-hydroxycarboxylate, and
    the (meth)acrylic acid obtained by dehydration of the α-hydroxycarboxylic acid is the same as or different from the (meth)acrylic acid transesterified with the alkyl α-hydroxycarboxylate.

2. The process according to claim 1, wherein the alkyl α-hydroxycarboxylate is obtained by alcoholysis of a hydroxycarboxamide.

3. The process according to claim 2, wherein the hydroxycarboxamide is obtained by a hydrolysis of a cyanohydrin.

4. The process according to claim 3, wherein the cyanohydrin is acetone cyanohydrin.

5. The process according to claim 3 wherein a catalyst is used for the hydrolysis.

6. The process according to claim 5, wherein the catalyst comprises manganese oxide, sulphuric acid or an enzyme.

7. The process according to claim 2, wherein the alcohol used for the alcoholysis of the hydroxycarboxamide comprises 1 to 10 carbon atoms.

8. The process according to claim 7, wherein the alcohol is methanol and/or ethanol.

9. The process according to claim 2, wherein the alcoholysis is carried out at a temperature in the range of 160-240° C.

10. The process according to claim 2, wherein the alcoholysis is carried out at a pressure in the range from 5 to 30 bar.

11. The process according to claim 2, wherein at least one basic catalyst is used for the alcoholysis.

12. The process according to claim 1, wherein the transesterification of the alkyl α-hydroxycarboxylate with (meth)acrylic acid is catalysed by an acid.

13. The process according to claim 12, wherein the acid is an ion exchanger.

14. The process according to claim 12, wherein the transesterification is carried out in a still.

15. The process according to claim 1, wherein the transesterification of the alkyl α-hydroxycarboxylate with (meth)acrylic acid is carried out at a pressure in the range from 100 mbar to 3 bar.

16. The process according to claim 1, wherein the transesterification of the alkyl α-hydroxycarboxylate with (meth)acrylic acid is carried out at a temperature in the range from 70 to 130° C.

17. The process according to claim 1, wherein a molar ratio of water to the alkyl α-hydroxycarboxylate is from 0.2 to 1.00.

18. The process according to claim 1, wherein the molar ratio of alkyl α-hydroxycarboxylate to (meth)acrylic acid in the transesterification of the alkyl α-hydroxycarboxylate with (meth)acrylic acid is in the range from 3:1 to 1:3.

19. The process according to claim 1, wherein the reaction time in the transesterification of the alkyl α-hydroxycarboxylate with (meth)acrylic acid is in the range from 5 minutes to 5 hours.

20. The process according to claim 1, wherein the dehydration of the α-hydroxycarboxylic acid and the transesterification of the alkyl α-hydroxycarboxylate with (meth)acrylic acid is carried out at the same pressure.

21. The process according to claim 1, wherein the (meth)acrylic acid obtained in gaseous form by the dehydration of the α-hydroxycarboxylic acid is passed to the transesterification without condensation and reevaporation.

22. A process for preparing alkyl (meth)acrylates, comprising
    transesterifying an alkyl α-hydroxycarboxylate with (meth)acrylic acid to obtain alkyl (meth)acrylates and α-hydroxycarboxylic acid, and
    dehydrating the α-hydroxycarboxylic acid to obtain (meth)acrylic acid,
    wherein
    the transesterification comprises from 0.1 to 50% water by weight relative to the alkyl α-hydroxycarboxylate, and
    the alkyl α-hydroxycarboxylate is obtained by alcoholysis of a hydroxycarboxamide.

* * * * *

UNITED STATES PATENT AND TRADEMARK OFFICE
CERTIFICATE OF CORRECTION

PATENT NO. : 7,999,130 B2  Page 1 of 1
APPLICATION NO. : 11/915042
DATED : August 16, 2011
INVENTOR(S) : Jochen Ackermann et al.

It is certified that error appears in the above-identified patent and that said Letters Patent is hereby corrected as shown below:

On the title page, Item (56), "U.S. Appl. No. 12/442,215, filed Mar. 23, 2009, Vogel, et al." should read -- U.S. Appl. No. 12/442,415, filed Mar. 23, 2009, Vogel, et al. --.

Signed and Sealed this
Twenty-ninth Day of November, 2011

David J. Kappos
*Director of the United States Patent and Trademark Office*